United States Patent
Schilling et al.

(10) Patent No.: US 10,449,364 B2
(45) Date of Patent: Oct. 22, 2019

(54) PACEMAKER MEDIATED TACHYCARDIA DETECTION AND INTERVENTION

(71) Applicant: Medtronic, Inc., Minneapolis, MN (US)

(72) Inventors: Eric A Schilling, Ham Lake, MN (US); Robert A Betzold, Fridley, MN (US); Greggory R Herr, Blaine, MN (US)

(73) Assignee: Medtronic, Inc., Minneapolis, MN (US)

(*) Notice: Subject to any disclaimer, the term of this patent is extended or adjusted under 35 U.S.C. 154(b) by 169 days.

(21) Appl. No.: 15/499,692

(22) Filed: Apr. 27, 2017

(65) Prior Publication Data

US 2018/0117324 A1    May 3, 2018

Related U.S. Application Data

(60) Provisional application No. 62/414,375, filed on Oct. 28, 2016, provisional application No. 62/468,319, filed on Mar. 7, 2017.

(51) Int. Cl.
| | | |
|---|---|---|
| *A61N 1/362* | (2006.01) | |
| *A61N 1/365* | (2006.01) | |
| *A61N 1/05* | (2006.01) | |
| *A61N 1/368* | (2006.01) | |

(52) U.S. Cl.
CPC ............ *A61N 1/3622* (2013.01); *A61N 1/365* (2013.01)

(58) Field of Classification Search
CPC ...... A61N 1/3622; A61N 1/365; A61N 1/056; A61N 1/36507; A61N 1/3682
See application file for complete search history.

(56) References Cited

U.S. PATENT DOCUMENTS

| | | |
|---|---|---|
| 4,374,382 A | 2/1983 | Markowitz |
| 4,401,119 A | 8/1983 | Herpers |
| 4,539,991 A | 9/1985 | Boute et al. |
| 4,554,920 A | 11/1985 | Baker, Jr. et al. |
| 4,712,556 A | 12/1987 | Baker, Jr. |
| 4,788,980 A | 12/1988 | Mann et al. |

(Continued)

FOREIGN PATENT DOCUMENTS

| | | |
|---|---|---|
| EP | 1009479 A1 | 6/2000 |
| WO | 01/24874 A1 | 4/2001 |
| WO | 2012082937 A2 | 6/2012 |

OTHER PUBLICATIONS (PCT/US2017/058696) PCT Notification of Transmittal of the International Search Report and the Written Opinion of the International Searching Authority, dated Feb. 27, 2018, 11 pages.

(Continued)

*Primary Examiner* — Lindsey G Wehrheim

(57) ABSTRACT

A method of employing an implantable medical device to detect pacemaker mediated tachycardia (PMT) and adjusting a parameter (e.g. PVARP) in response to confirmation of the PMT. The method comprises, with a processor located in the implantable medical device, (1) measuring a first Vp-As (VA1), (2) lengthening SAV by 50 ms for 1 beat in response to measuring VA1, (3) measuring a second Vp-As (VA2), (4) returning to a normal SAV, (5) measuring a third Vp-As (VA3), (6) determining whether VA1=VA2 and VA1=VA3, (7) in response to determining whether VA1=VA2 and VA1=VA3, confirming presence of PMT, and (8) in response to confirming presence of PMT, PVARP is extended.

23 Claims, 9 Drawing Sheets

(56) References Cited

U.S. PATENT DOCUMENTS

| | | |
|---|---|---|
| 5,117,824 A | 6/1992 | Keimel et al. |
| 5,193,550 A | 3/1993 | Duffin |
| 5,228,438 A | 7/1993 | Buchanan |
| 5,247,929 A | 9/1993 | Stoop et al. |
| 5,312,450 A | 5/1994 | Markowitz |
| 5,423,868 A | 6/1995 | Nappholz et al. |
| 5,496,350 A | 3/1996 | Lu |
| 5,507,783 A | 4/1996 | Buchanan |
| 5,514,164 A | 5/1996 | Mann et al. |
| 5,545,186 A | 8/1996 | Olson et al. |
| 5,674,255 A | 10/1997 | Walmsley et al. |
| 5,755,736 A | 5/1998 | Gillberg et al. |
| 6,285,908 B1 | 9/2001 | Mann et al. |
| 6,564,095 B1 | 5/2003 | Stahl et al. |
| 7,551,961 B1 | 6/2009 | Pei et al. |
| 7,986,994 B2 | 7/2011 | Stadler et al. |
| 9,242,101 B2 | 1/2016 | Ip et al. |
| 9,511,233 B2 | 12/2016 | Sambelashvili |
| 2004/0210264 A1 | 10/2004 | Kleckner et al. |
| 2004/0210266 A1 | 10/2004 | Kramer |
| 2006/0089676 A1 | 4/2006 | Rottenberg et al. |
| 2007/0244521 A1 | 10/2007 | Bornzin et al. |
| 2008/0269826 A1 | 10/2008 | Lian et al. |
| 2010/0286743 A1 | 11/2010 | Enrooth et al. |
| 2015/0142069 A1 | 5/2015 | Sambelashvili |

OTHER PUBLICATIONS

Strik, M. Md. PhD., et al. "Accuracy of the Pacemaker-Mediated Tachycardia Algorithm in Boston Scientific Devices", Journal of Electrocardiology 49 (2016) 522-529, www.jecgonline.com, www.sciencedirect.com, 8 pages.

PACEMAKER MEDIATED TACHYCARDIA DETECTION AND INTERVENTION

CROSS-REFERENCE TO RELATED APPLICATIONS

This application claims the benefit of U.S. Provisional Application No. 62/414,375, filed on Oct. 28, 2016 and U.S. Provisional Application No. 62/468,319 filed Mar. 7, 2017. The disclosures of the above applications are incorporated herein by reference in their entirety.

TECHNICAL FIELD

The present disclosure relates to detection of pacemaker mediated tachycardia (PMT), and, more particularly, adjusting operation of an implantable device to eliminate, terminate or reduce PMT.

BACKGROUND

A pacemaker-mediated tachycardia (PMT), also referred to as endless loop tachycardia, occurs when a pacemaker paces the ventricles at inappropriately fast rates for sustained periods of time. PMT occurs when a ventricular event occurs at a time during which the connective tissue between the atrium and ventricle can transmit retrograde electrical signals from the ventricle to the atrium. The conduction of the ventricular signal to the atrium provides a spurious electrical signal in the atrium that is considered to be a natural atrial event by the pacemaker. The pacemaker senses the spurious retrograde atrial signal and then paces the ventricle at a programmed AV time period following the signal. The paced ventricular signal is conducted to the atrium and is again erroneously detected by the pacemaker as a natural atrial event. The pacemaker therefore continues to pace the ventricle at a relatively high rate defined by the sum of the programmed AV interval and the retrograde conduction time between the ventricle and atrium. The high rate is sustained indefinitely by the pacemaker, because retrograde conduction ensures that the pacemaker detects what appear to be high rate atrial events and tracks these spurious atrial events by generating corresponding high rate ventricular paces.

PMT can be caused by retrograde conduction following a premature ventricular contractions (PVC), a right ventricular (RV) pace can produce retrograde conduction back up to the atrium. In response to the retrograde conduction, an atrial sensed event to be detected by the implanted device which in turn causes an RV pace to be deliver at the programmed sensed atrioventricular (SAV) interval. This produces a cycle of inappropriately fast pacing by the device called PMT, as described in U.S. Pat. No. 4,554,920 to Baker et. al.

Existing algorithms for detection of PMT may be able to achieve improved PMT detection, especially for patients experiencing high intrinsic rates. High intrinsic rates can lead to inappropriate PMT intervention (e.g. extending postventricular atrial refractory period (PVARP) for one cycle) which can lead to dropped beats or the interruption of CRT pacing. It is therefore desirable to develop devices and methods that are configured to avoid, eliminate, terminate or reduce PMTs.

SUMMARY

The present disclosure employs an implantable medical device that is configured to confirm whether a pacemaker-mediated tachycardia (PMT) has been detected. PMT confirmation involves periodic extensions to sensed atrioventricular (SAV) intervals and measurement of the resulting ventricular atrial (VA) intervals. If the ventricular atrial (VA) interval is unchanged, PMT is confirmed. If the VA interval changes, a true PMT is not present.

The algorithm of the present disclosure adds a confirmation phase to an existing PMT detection algorithm. During the confirmation phase, if lengthening the SAV does not change the ventricular pace-atrial sense (Vp-As) interval, PMT is confirmed. An exemplary method implemented by a medical device comprises, with a processor. The processor performs a variety of functions including all of the measuring, timing and adjusting of intervals. For example, the processor, executing instructions, implements a measurement cycle that involves (1) measuring Vp-As (VA1), (2) lengthening SAV by 50 ms for 1 beat, (3) measuring Vp-As (VA2), (3) returning to a normal SAV, (4) measuring Vp-As (VA3), (5) if VA1 does not equal VA2, then PMT is not confirmed. Alternatively, if VA1=VA2, a PMT is confirmed. The measurement cycle is repeated a number of times (e.g. two times (6 more beats)) to confirm detection of PMT. In response to PMT being confirmed, the PVARP duration is extended to 400 ms for 1 beat as shown in FIG. 7.

One or more embodiments relate to a method of employing an implantable medical device to detect pacemaker mediated tachycardia (PMT) and adjusting a parameter (e.g. post-ventricular atrial refractory period (PVARP)) in response to detection of the PMT. The method comprises, with a processor located in the implantable medical device, (1) measuring a first Vp-As (VA1), (2) lengthening SAV by 50 ms for 1 beat in response to measuring VA1, (3) measuring a second Vp-As (VA2), (4) returning to a normal SAV, (5) measuring a third Vp-As (VA3), (6) determining whether VA1=VA2 and VA1=VA3, (7) in response to determining whether VA1=VA2 and VA1=VA3, presence of PMT is confirmed, and (8) in response to confirming presence of PMT, PVARP is extended.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION

Exemplary systems, methods, and interfaces shall be described with reference to FIGS. 1-8. FIGS. 5-8 and the accompanying text describe the manner in which PMTs are confirmed. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Figure 1:
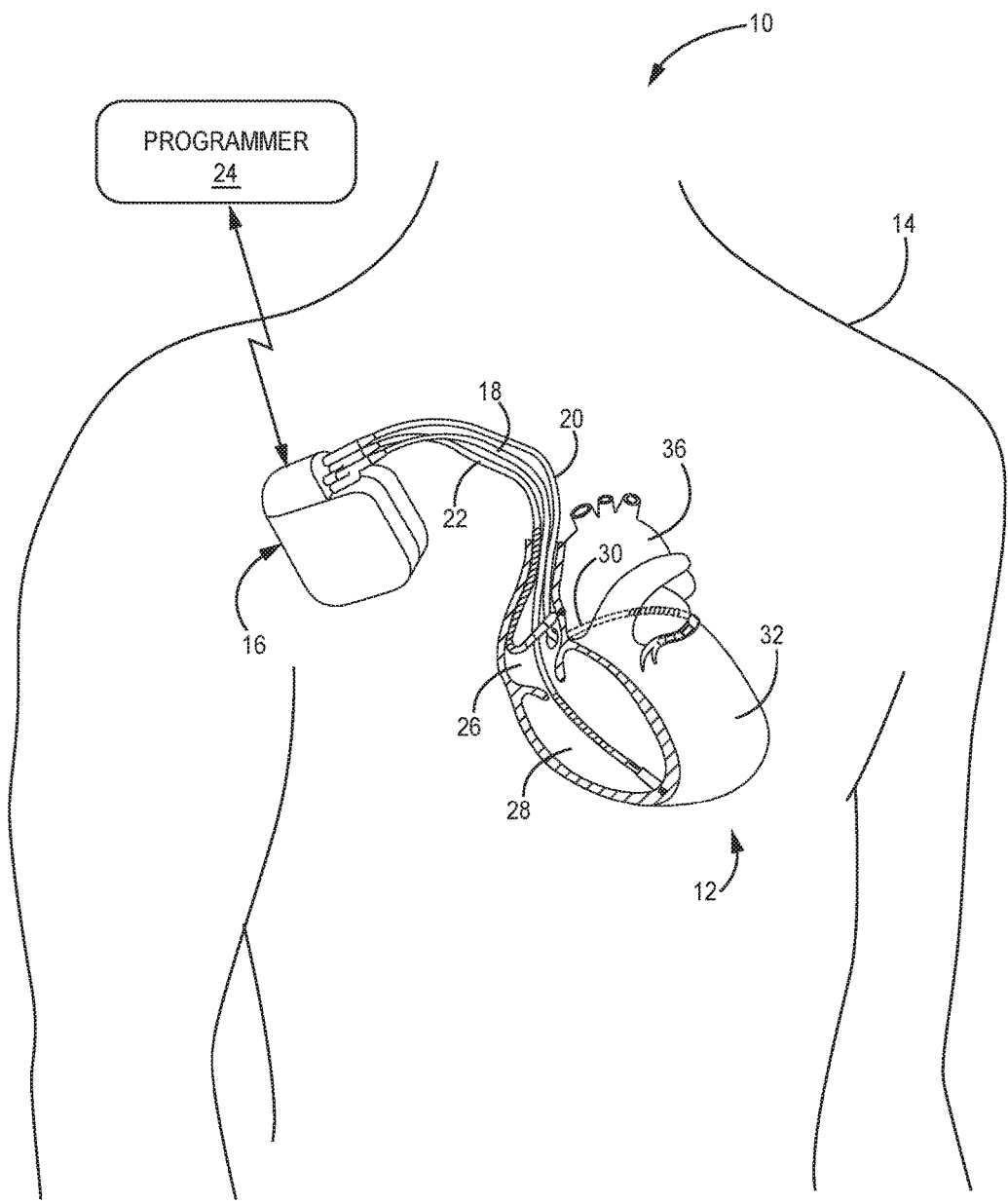
FIG. 1 is a conceptual drawing illustrating an example system configured to transmit diagnostic information indicative of heart failure that includes an implantable medical device (IMD) coupled to implantable medical leads.

FIG. 1 is a conceptual drawing of an example, system 10 includes IMD 16, which is coupled to leads 18, 20, and 22 and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily a human patient.

In general, the techniques described in this disclosure may be implemented by any medical device, e.g., implantable or external, that senses a signal indicative of cardiac activity, patient 14 activity, and/or fluid volume within patient 14. In the example of FIG. 1, leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10 may additionally or alternatively include one or more leads or lead segments (not shown in FIG. 1) that deploy one or more electrodes within the vena cava, or other veins. Furthermore, in some examples, system 10 may additionally or alternatively include temporary or permanent epicardial or subcutaneous leads with electrodes implanted outside of heart 12, instead of or in addition to transvenous, intracardiac leads 18, 20 and 22. Such leads may be used for one or more of cardiac sensing, pacing, or cardioversion/defibrillation. For example, these electrodes may allow alternative electrical sensing configurations that provide improved or supplemental sensing in some patients.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In addition, IMD 16 may monitor the electrical signals of heart 12 for patient metrics stored in IMD 16 and/or used in generating the heart failure risk level. IMD 16 may utilize two of any electrodes carried on leads 18, 20, 22 to generate electrograms of cardiac activity. In some examples, IMD 16 may also use a housing electrode of IMD 16 (not shown) to generate electrograms and monitor cardiac activity. Although these electrograms may be used to monitor heart 12 for potential arrhythmias and other disorders for therapy, the electrograms may also be used to monitor the condition of heart 12. For example, IMD 16 may monitor heart rate (night time and day time), heart rate variability, ventricular or atrial intrinsic pacing rates, indicators of blood flow, or other indicators of the ability of heart 12 to pump blood or the progression of heart failure.

IMD 16 may also communicate with external programmer 24. In some examples, programmer 24 comprises an external device, e.g., a handheld computing device, computer workstation, or networked computing device. Programmer 24 may include a user interface that receives input from a user. In other examples, the user may also interact with programmer 24 remotely via a networked computing device. The user may interact with programmer 24 to communicate with IMD 16. For example, the user may interact with programmer 24 to send an interrogation request and retrieve patient metrics or other diagnostic information from IMD 16. A user may also interact with programmer 24 to program IMD 16, e.g., select values for operational parameters of IMD 16. Although the user is a physician, technician, surgeon, electrophysiologist, or other healthcare professional, the user may be patient 14 in some examples.

As another example, the user may use programmer 24 to retrieve information from IMD 16 regarding the performance or integrity of IMD 16 or other components of system 10, such as leads 18, 20 and 22, or a power source of IMD 16. In some examples, any of this information may be presented to the user as an alert (e.g., a notification or instruction). Further, alerts may be pushed from IMD 16 to facilitate alert delivery whenever programmer 24 is detectable by IMD 16. IMD 16 may wirelessly transmit alerts, or other diagnostic information, to facilitate immediate notification of the heart failure condition.

IMD 16 and programmer 24 may communicate via wireless communication using any techniques known in the art. Examples of communication techniques may include, for example, radiofrequency (RF) telemetry, but other communication techniques such as magnetic coupling are also contemplated. In some examples, programmer 24 may include a programming head that may be placed proximate to the body of the patient near the IMD 16 implant site in order to improve the quality or security of communication between IMD 16 and programmer 24.

IMD 16 may automatically detect each of the patient metrics and store them within the IMD for later transmission. Although IMD 16 may automatically detect a number (e.g. 10 or less) different patient metrics in some examples, IMD 16 may detect more or less patient metrics in other examples. For example, the patient metrics may include tachycardia, an atrial fibrillation duration, a ventricular contraction rate during atrial fibrillation, a patient activity, a nighttime heart rate, a heart rate variability, a cardiac resynchronization therapy (CRT) percentage (e.g., the percentage of cardiac cycles for which cardiac resynchronization pacing was provided), or the occurrence of or number of therapeutic electrical shocks. The metric-specific thresholds may include an atrial fibrillation duration threshold of approximately 6 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, or an electrical shock threshold of 1 electrical shock.

Figure 2A:
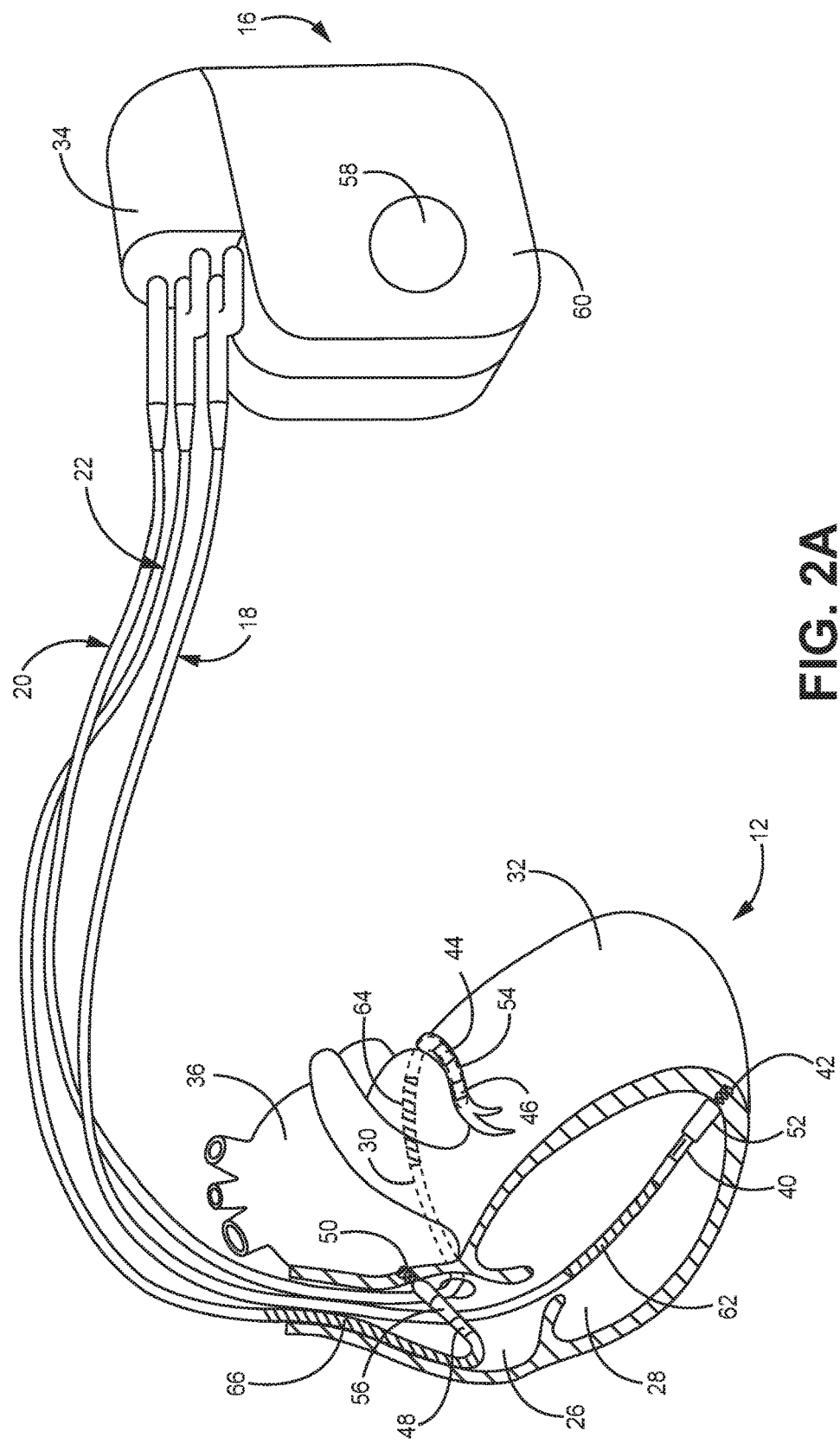
FIG. 2A is a conceptual drawing illustrating the example IMD and leads of FIG. 1 in conjunction with a heart.

FIG. 2A is a conceptual drawing illustrating IMD 16 and leads 18, 20, and 22 of system 10 in greater detail. As shown in FIG. 2A, IMD 16 is coupled to leads 18, 20, and 22. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2A, IMD 16 includes one or more housing electrodes, such as housing electrode 58, which may be formed integrally with an outer surface of hermetically-sealed housing 60 of IMD 16, or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration or electrode vector.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of system 10 illustrated in FIGS. 1 and 2A is merely one example. In other examples, a system may include epicardial leads and/or subcutaneous electrodes instead of or in addition to the transvenous leads 18, 20, 22 illustrated in FIG. 1. Yet another alternative configuration that may implement teachings of the present disclosure relates to a subcutaneous device with a substernal lead, as shown and described relative to U.S. patent application Ser. No. 14/173,328, the disclosure of which is incorporated by reference in its entirety. Further, IMD 16 need not be implanted within patient 14. In examples in which IMD 16 is not implanted in patient 14, IMD 16 may sense electrical signals and/or deliver defibrillation pulses and other therapies to heart 12 via percutaneous leads that extend through the skin of patient 14 to a variety of positions within or outside of heart 12.

Figure 2B:
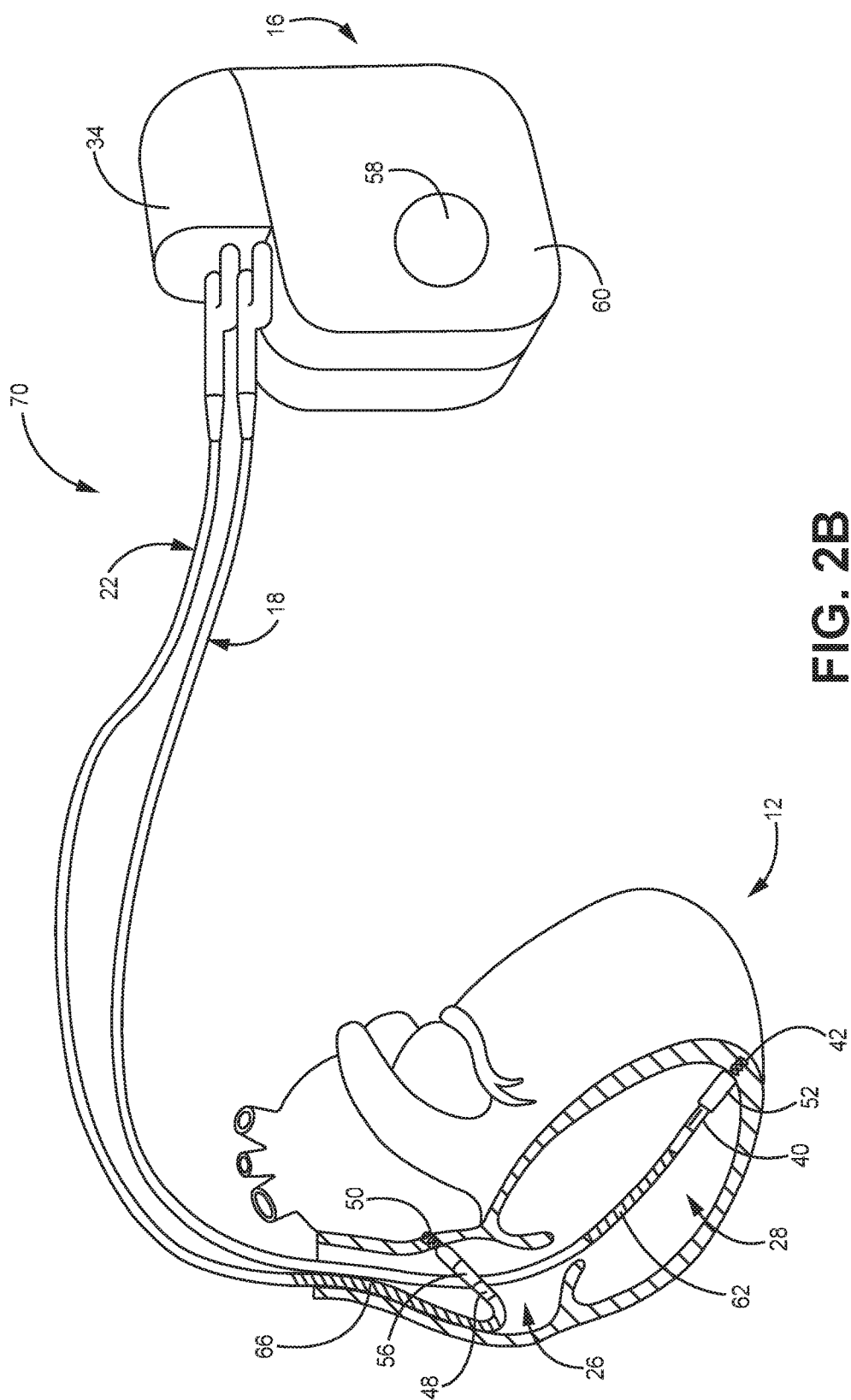
FIG. 2B is a conceptual drawing illustrating the example IMD of FIG. 1 coupled to a different configuration of implantable medical leads in conjunction with a heart.

In addition, in other examples, a system may include any suitable number of leads coupled to IMD 16, and each of the leads may extend to any location within or proximate to heart 12. For example, systems in accordance with this disclosure may include three transvenous leads located as illustrated in FIGS. 1 and 2, and an additional lead located within or proximate to left atrium 36. As another example, systems may include a single lead that extends from IMD 16 into right atrium 26 or right ventricle 28, or two leads that extend into a respective one of the right ventricle 26 and right atrium 26. An example of a two lead type of system is shown in FIG. 2B. Any electrodes located on these additional leads may be used in sensing and/or stimulation configurations.

Any of electrodes 40, 42, 44, 46, 48, 50, 62, 64, 66, and 58 may be utilized by IMD 16 to sense or detect patient metrics used to generate the heart failure risk level for patient 14. Typically, IMD 16 may detect and collect patient metrics from those electrode vectors used to treat patient 14.

For example, IMD 16 may derive an atrial fibrillation duration, heart rate, and heart rate variability metrics from electrograms generated to deliver pacing therapy. However, IMD 16 may utilize other electrodes to detect these types of metrics from patient 14 when other electrical signals may be more appropriate for therapy.

In addition to electrograms of cardiac signals, any of electrodes 40, 42, 44, 46, 48, 50, 62, 64, 66, and 58 may be used to sense non-cardiac signals. For example, two or more electrodes may be used to measure an impedance within the thoracic cavity of patient 14. For example, coil electrode 62 and housing electrode 58 may be used as the sensing vector for intrathoracic impedance because electrode 62 is located within RV 28 and housing electrode 58 is located at the IMD 16 implant site generally in the upper chest region. However, other electrodes spanning multiple organs or tissues of patient 14 may also be used, e.g., an additional implanted electrode used only for measuring thoracic impedance.

FIG. 2B is a conceptual diagram illustrating another example system 70, which is similar to system 10 of FIGS. 1 and 2A, but includes two leads 18, 22, rather than three leads. Leads 18, 22 are implanted within right ventricle 28 and right atrium 26, respectively. System 70 shown in FIG. 2B may be useful for physiological sensing and/or providing pacing, cardioversion, or other therapies to heart 12. Detection of patient diagnostic data according to this disclosure may be performed in two lead systems in the manner described herein with respect to three lead systems. In other examples, a system similar to systems 10 and 70 may only include one lead (e.g., any of leads 18, 20 or 22) to deliver therapy and/or sensor and detect patient metrics related to monitoring risk of heart failure. Alternatively, diagnostic data may be implemented in systems utilizing subcutaneous leads, subcutaneous IMDs, or even external medical devices. Although FIGS. 1-2 provide some useful IMD 16 implantation examples, skilled artisans appreciate that IMD 16 and its associated electrodes can be implanted in other locations of the body and can include leads or be leadless.

Figure 3:
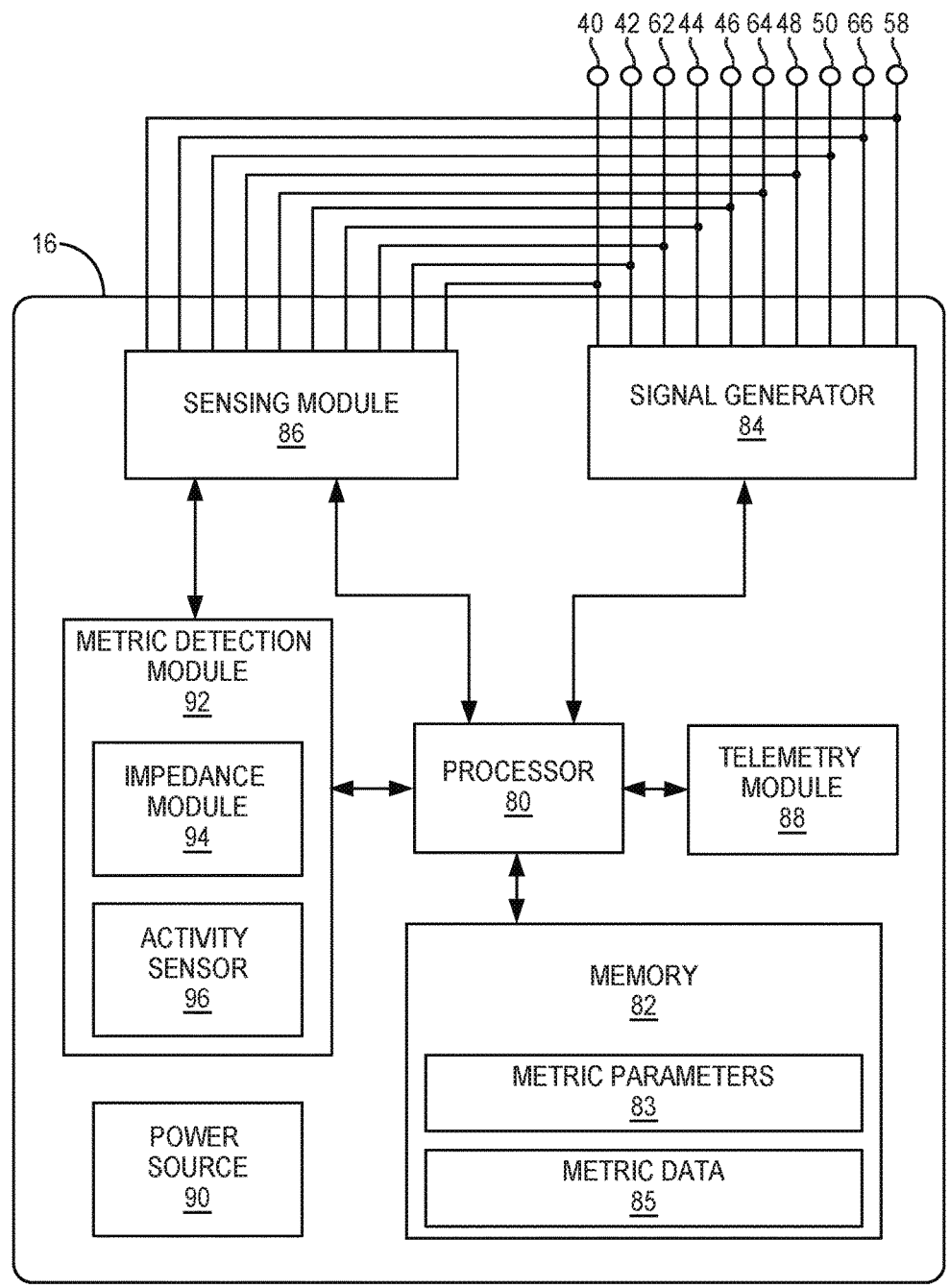
FIG. 3 is a functional block diagram illustrating an example configuration of the IMD of FIG. 1.
Figure 7:
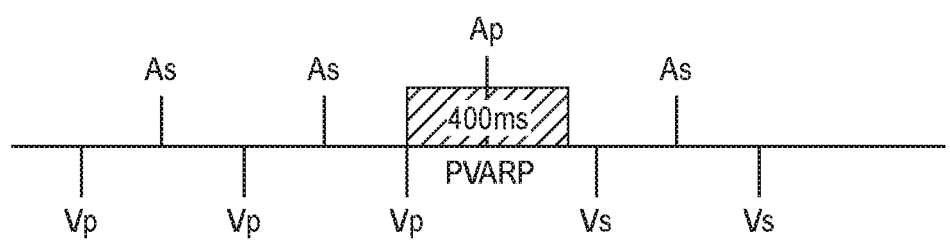
FIG. 7 depicts a simplified event timing diagram in which PVARP duration is extended to 400 ms for 1 beat.

FIG. 3 is a functional block diagram illustrating an example configuration of IMD 16. In the illustrated example, IMD 16 includes a processor 80, memory 82, metric detection module 92, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. The processor 80 performs a variety of functions including all of the measuring, timing and adjusting of intervals. For example, the processor, executing instructions, causes a measurement cycle to be implemented that involves (1) measuring Vp-As (VA1), (2) lengthening SAV by 50 ms for 1 beat, (3) measuring Vp-As (VA2), (3) returning to a normal SAV, (4) measuring Vp-As (VA3), (5) if VA1 does not equal VA2, then PMT is not confirmed. Alternatively, if VA1=VA2, a PMT is confirmed. The measurement cycle is repeated a number of times (e.g. two times (6 more beats)) to confirm detection of PMT. In response to PMT being confirmed, the PVARP duration is extended to 400 ms for 1 beat as shown in FIG. 7.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls signal generator 84 to deliver stimulation therapy to heart 12 according to a therapy parameters, which may be stored in memory 82. For example, processor 80 may control signal generator 84 to deliver electrical pulses with the amplitudes, pulse widths, frequency, or electrode polarities specified by the therapy parameters.

Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy (e.g. pacing pulses) to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12, impedance, or other electrical phenomenon. Sensing may be done to determine heart rates or heart rate variability, or to detect arrhythmias or other electrical signals. Sensing module 86 may also include a switch module to select which of the available electrodes are used to sense the heart activity, depending upon which electrode combination, or electrode vector, is used in the current sensing configuration. In some examples, processor 80 may select the electrodes that function as sense electrodes, i.e., select the sensing configuration, via the switch module within sensing module 86. Sensing module 86 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 80, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 80 may control the functionality of sensing module 86 by providing signals via a data/address bus.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR, CRT, and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

Interval counters implemented by the timing and control module of processor 80 may be reset upon sensing of R-waves and P-waves with detection channels of sensing module 86. In examples in which IMD 16 provides pacing, signal generator 84 may include pacemaker output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In such examples, processor 80 may reset the interval counters upon the generation of pacing pulses by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the timing and control module to control the operation of the escape interval counters therein and to define refractory periods during which detection of R-waves and P-waves is ineffective to restart the escape interval counters for the an anti-tachyarrhythmia pacing. Processor 80 detects data (e.g. data observations etc.) at an IMD 16 check and/or interrogation time point. Data is sensed based on signals from sensing module 86. Additionally, cardioversion or defibrillation shock can be determined to be needed based upon sensed data, and processor 80 may control the amplitude, form and timing of the shock delivered by signal generator 84. Memory 82 is configured to store data. Exemplary data can be associated with a variety of operational parameters, therapy parameters, sensed and detected data, and any other information related to the therapy and treatment of patient 14. In the example of FIG. 3, memory 82 also includes metric parameters 83 and metric data 85. Metric parameters 83 may include all of the parameters and instructions required by processor 80 and metric detection module 92 to sense and detect each of the patient metrics used to generate the diagnostic information transmitted by IMD 16. Metric data 85 may store all of the data generated from the sensing and detecting of each patient metric. In this manner, memory 82 stores a plurality of automatically detected patient metrics as the data required to generate a risk level of patient 14 being admitted to the hospital due to heart failure.

Metric parameters 83 may include definitions of each of the patient metrics automatically sensed or measured by metric detection module 92. These definitions may include instructions regarding what electrodes or sensors to use in the detection of each metric. Preferred metrics include an (1) impedance trend index (also referred to as OPTIVOL® commercially available in IMDs from Medtronic Inc., located in MN), (2) intrathoracic impedance, (3) atrial tachycardia/atrial fibrillation (AT/AF) burden, (4) mean ventricular rate during AT/AF, (5) patient activity, (6) V rate, (7) day and night heart rate, (8) percent CRT pacing, and/or (9) number of shocks. Impedance trend index is described with respect to U.S. Pat. No. 7,986,994, and assigned to the assignee of the present invention, the disclosure of which is incorporated by reference in its entirety herein. Other suitable metrics can also be used. For example, a reference or baseline level impedance is established for a patient from which subsequently acquired raw impedance data is compared. For example, raw impedance can be acquired from the electrodes (e.g. RV coil to Can) and compared to the reference impedance (also referred to as normal impedance or baseline impedance. Baseline impedance can be derived by averaging impedance over a duration of 7 days (1-week) to 90 days (3-months).

Metric parameters 83 may also store a metric-specific threshold for each of the patient metrics automatically detected by metric detection module 92. Metric thresholds may be predetermined and held constant over the entire monitoring of patient 14. In some examples, however, metric thresholds may be modified by a user during therapy or processor 80 may automatically modify one or more metric thresholds to compensate for certain patient conditions. For example, a heart rate threshold may be changed over the course of monitoring if the normal or baseline heart rate has changed during therapy.

In one example, these metric-specific thresholds may include a thoracic fluid index threshold of approximately 60, an atrial fibrillation burden threshold of approximately 6 consecutive hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, and an electrical shock number threshold of 1 electrical shock. These thresholds may be different in other examples, and may be configured by a user, e.g., a clinician, for an individual patient.

Metric data 85 is a portion of memory 82 that may store some or all of the patient metric data that is sensed and/or detected by metric detection module 92. Metric data 85 may store the data for each metric on a rolling basis during an evaluation window. The evaluation window may only retain recent data and delete older data from the evaluation window when new data enters the evaluation window. In this manner, the evaluation window may include only recent data for a predetermined period of time. In one or more other embodiments, memory can be configured for long term storage of data. Processor 80 may access metric data when necessary to retrieve and transmit patient metric data and/or generate heart failure risk levels. In addition, metric data 85 may store any and all data observations, heart failure risk levels or other generated information related to the heart failure risk of patient 14. The data stored in metric data 85 may be transmitted as part of diagnostic information. Although metric parameters 83 and/or metric data 85 may consist of separate physical memories, these components may simply be an allocated portion of the greater memory 82.

Metric detection module 92 may automatically sense and detect each of the patient metrics. Metric detection module 92 may then generate diagnostic data, e.g., data that indicates a threshold has been crossed, risk levels, based on the patient metrics. For example, metric detection module 92 may measure the thoracic impedance, analyze an electrogram of heart 12, monitor the electrical stimulation therapy delivered to patient 14, or sense the patient activity. It is noted that functions attributed to metric detection module 92 herein may be embodied as software, firmware, hardware or any combination thereof. In some examples, metric detection module 92 may at least partially be a software process executed by processor 80. In one example, metric detection module 92 may compare each of the patient metrics to their respective metric-specific thresholds defined in metric parameters 83 to generate the heart failure risk level. Metric detection module 92 may automatically detect two or more patient metrics. In other examples, metric detection module 92 may detect different patient metrics.

In one example, metric detection module 92 may analyze electrograms received from sensing module 86 to detect an atrial fibrillation or atrial tachycardia, and determine atrial tachycardia or fibrillation burden, e.g., duration, as well as a ventricular contraction rate during atrial fibrillation. Metric detection module 92 may also analyze electrograms in conjunction with a real-time clock, patient posture or activity signal, e.g., from activity sensor 96, and/or other physiological signals indicative of when a patient is asleep or awake to determine a nighttime (or sleeping) heart rate or a daytime (or awake) heart rate or a difference between the day and night heart rate, and also analyze electrograms to determine a heart rate variability, or any other detectable cardiac events from one or more electrograms. As described above, metric detection module 92 may use peak detection, interval detection, or other methods to analyze the electrograms.

In addition, metric detection module 92 may include and/or control impedance module 94 and activity sensor 96. Impedance module 94 may be used to detect the thoracic impedance used to generate the thoracic fluid index. As described herein, impedance module 94 may utilize any of the electrodes of FIG. 1, 2 or 3 to take intrathoracic impedance measurements. In other examples, impedance module 94 may utilize separate electrodes coupled to IMD 16 or in wireless communication with telemetry module 88. Once impedance module 94 measures the intrathoracic impedance of patient 14, metric detection module 92 may generate the thoracic fluid index and compare the index to the thoracic fluid index threshold defined in metric parameters 83.

Activity sensor 96 may include one or more accelerometers or other devices capable of detecting motion and/or position of patient 14. Activity sensor 96 may therefore detect activities of patient 14 or postures engaged by patient 14. Metric detection module 92 may, for example, monitor the patient activity metric based on the magnitude or duration of each activity and compare the determined metric data to the activity threshold defined in metric parameters 83. In addition to detecting events of patient 14, metric detection module 92 may also detect certain therapies delivered by signal generator 84, e.g., as directed by processor 80. Metric detection module 92 may monitor signals through signal generator 84 or receive therapy information directly from processor 80 for the detection. Example patient metrics detected by this method may include a cardiac resynchronization therapy percentage or metrics related to delivery of electrical shocks.

The cardiac resynchronization therapy (CRT) metric may be the amount or percentage of time each day, or an amount of percentage of cardiac cycles, as examples, that IMD 16 delivers cardiac resynchronization therapy to heart 12. Low CRT amounts or percentages may indicate that beneficial therapy is not being effectively delivered and that adjustment of therapy parameters, e.g., an atrioventricular delay or a lower pacing rate, may improve therapy efficacy. In one example, higher CRT amounts or percentages may indicate that heart 12 is sufficiently pumping blood through the vasculature with the aid of therapy to prevent fluid buildup. In examples of other types of cardiac pacing (non-CRT) or stimulation therapy, higher therapy percentages may indicate that heart 12 is unable to keep up with blood flow requirements.

An electrical shock may be a defibrillation event or other high energy shock used to return heart 12 to a normal rhythm. The metric related electrical shocks may be a number or frequency of electrical shocks, e.g., a number of shocks within a period of time. Metric detection module 92 may detect these patient metrics as well and compare them to a cardiac resynchronization therapy percentage and shock event threshold, respectively, defined in metric parameters 83 to determine when each patient metric has become critical. In one example, the electrical shock event metric may become critical when a threshold number of shocks is delivered, e.g., within a time period, or even when patient 14 even receives one therapeutic shock.

Metric detection module 92 may include additional sub-modules or sub-routines that detect and monitor other patient metrics used to monitor patient 14 and/or generate the HF event (e.g. HFH) risk level. In some examples, metric detection module 92, or portions thereof, may be incorporated into processor 80 or sensing module 86. In other examples, raw data used to produce patient metric data may be stored in metric data 85 for later processing or transmission to an external device. An external device may then produce each patient metric from the raw data, e.g., electrogram or raw intrathoracic impedance which is subsequently compared to a reference impedance. In other examples, metric detection module 92 may additionally receive data from one or more implanted or external devices used to detect each metric which IMD 16 may store as metric data.

In some examples, the patient metric thresholds used to generate the risk levels may change over time, e.g., the patient metric thresholds may either be modified by a user or automatically changed based on other patient conditions. Telemetry module 88 may receive commands from programmer 24, for example, to modify one or more metric parameters 83 (e.g., metric creation instructions or metric-specific thresholds). In some examples, processor 80 may automatically adjust a metric-specific threshold if certain conditions are present in patient 14. For example, the threshold may be adjusted if patient 14 is experiencing certain arrhythmias or data contained in cardiac electrograms change, e.g., there is a deviation in ST elevations or presence of premature ventricular contractions, in such a manner that requires a change in the threshold.

As described above, processor 80 may provide an alert to a user, e.g., of programmer 24, regarding the data from any patient metric and/or the HF event risk level. In one example, processor 80 may provide an alert with the HFH risk level when programmer 24 or another device communicates with IMD 16. Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer. In some examples, processor 80 may transmit atrial and ventricular heart signals, e.g., EGMs, produced by atrial and ventricular sense amplifier circuits within sensing module 86 to programmer 24.

Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician. In this manner, a computing device or user interface of the network may be the external computing device that delivers the alert, e.g., patient metric data. In other examples, one or more steps in the generation of the heart failure risk level may occur within a device external of patient 14, e.g., within programmer 24 or a server networked to programmer 24. In this manner, IMD 16 may detect and store patient metrics before transmitting the patient metrics to a different computing device.

Processor 80 may control telemetry module 88 to transmit diagnostic information to a clinician or other user. If one of the automatically detected patient metrics exceeds its respective metric-specific threshold, processor 80 may control telemetry module to transmit that patient metric and possibly other patient metrics to allow the clinician to more accurately diagnose the problem with patient 14.

Figure 4:
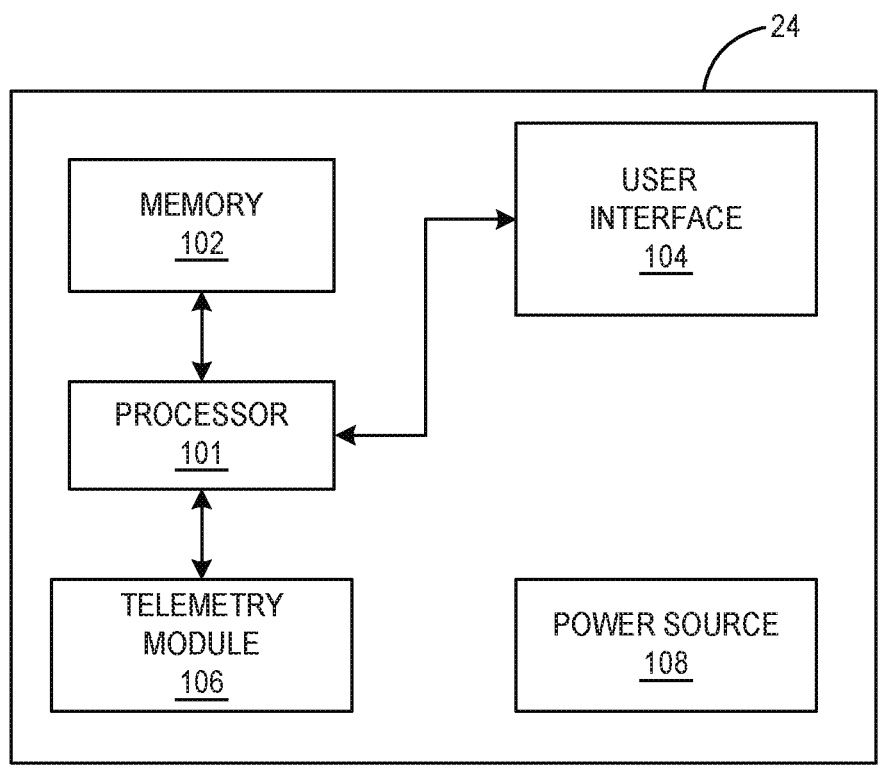
FIG. 4 is a functional block diagram illustrating an example configuration of an external programmer that facilitates user communication with the IMD.

FIG. 4 is a functional block diagram illustrating an example configuration of external programmer 24. As shown in FIG. 4, programmer 24 may include a processor 101, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to configure the operational parameters of and retrieve data from IMD 16 (FIG. 1). The clinician may interact with programmer 24 via user interface 104, which may include display to present graphical user interface to a user, and a keypad or another mechanism for receiving input from a user. In addition, the user may receive an alert or notification from IMD 16 indicating the heart failure risk level and/or patient metrics via programmer 24. In other words, programmer 24 may receive diagnostic information from IMD 16.

Processor 101 can take the form one or more microprocessors, DSPs, ASICs, FPGAs, programmable logic circuitry, or the like, and the functions attributed to processor 101 herein may be embodied as hardware, firmware, software or any combination thereof. Memory 102 may store instructions that cause processor 101 to provide the functionality ascribed to programmer 24 herein, and information used by processor 101 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In this manner, telemetry module 106 may transmit an interrogation request to telemetry module 88 of IMD 16. Accordingly, telemetry module 106 may receive data (e.g. diagnostic information, real-time data related to tachycardia, etc.) or diagnostic information selected by the request or based on already entered patient status to IMD 16. The data may include patient metric values or other detailed information from telemetry module 88 of IMD 16. The data may include an alert or notification of the heart failure risk level from telemetry module 88 of IMD 16. The alert may be automatically transmitted, or pushed, by IMD 16 when the heart failure risk level becomes critical. In addition, the alert may be a notification to a healthcare professional, e.g., a clinician or nurse, of the risk level and/or an instruction to patient 14 to seek medical treatment for the potential heart failure condition that may require re-hospitalization is left untreated. In response to receiving the alert, user interface 104 may present the alert to the healthcare professional regarding the risk level or present an instruction to patient 14 to seek medical treatment.

Figure 5:
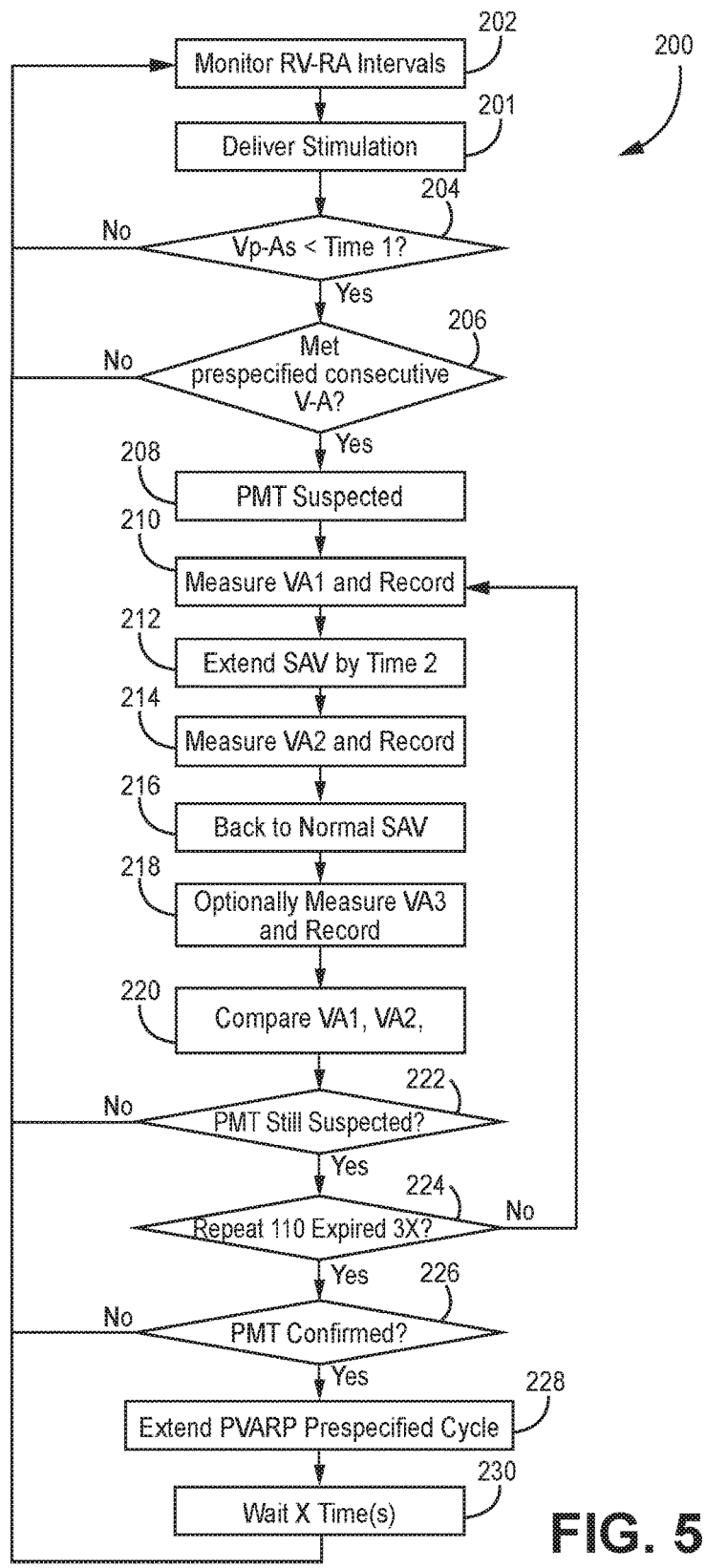
FIG. 5 depicts a flowchart of a method implemented by an implantable medical device disclosed herein that confirms whether a PMT has been detected.

The exemplary methods and/or devices described herein may track, or monitor, atrial and/or ventricular events (e.g., activation times such as right ventricular activation time, left ventricular activation time, atrial activation times or paced events etc.) to determine whether an actual PMT has been confirmed to be present in the monitored events. Once a PMT has been confirmed to be present, post-ventricular atrial refractory period (PVARP) can be adjusted. For example, the duration of PVARP can be extended or increased. Extending PVARP ensures proper timing is occurring between the atrial and ventricular events thereby allowing the heart to return to normal rhythm. One manifestation of the basic logical flow can be seen in exemplary method 200 of FIG. 5. FIG. 5 and the accompanying text is directed to an IMD 16, implementing method 200, to confirm whether a PMT has been detected. Generally, a PMT is detected when lengthening the SAV does not substantially change the ventricular pace (Vp)-atrial sense (As) interval. In response to actual confirmation of PMT, PVARP duration is extended (e.g. from 300 ms to 400 ms) to ensure the atrial event occurs during PVARP. An exemplary atrial event occurring during PVARP is shown as Ar in FIG. 7.

Method 200 begins at block 202 in which RV-RA intervals are monitored using electrodes, for sensing heart activity, located on the RV and RA leads 18, 22, respectively. For example, the RV lead 18 includes an electrode to sense heart activity from the RV while RA lead 22 includes an electrode to sense heart activity from the RA. LV lead 20 also includes electrodes to sense heart activity emanating from the left ventricle.

At block 201, ventricular pacing pulses are generated by the IMD 16 pulse generator and delivered through the LV lead 20 to the left ventricle in order to start measuring intervals and sense the atrial depolarizations. Skilled artisans appreciate that pacing pulses can be either solely delivered to the left ventricle (also referred to as monoventricular pacing or fusion pacing) or biventricular pacing pulses are delivered to the left and right ventricles.

At block 204, the processor for IMD 16 determines whether Vp-As<Time1. An exemplary Time1 can be set at 400 milliseconds (ms). Alternatively, Time1 can be customized to each patient based upon historical data acquired by the IMD 16 for the patient and/or other suitable means. If the IMD 16 processor 80 determines Vp-As<Time1, then the YES path from block 204 continues to block 206. In contrast, if the IMD 16 processor determines Vp-As is not less than Time1, then the NO path from block 204 continues to block 202 to continue monitoring RV-RA intervals.

At block 206, the IMD 16 processor determines whether a pre-specified consecutive number of V-A intervals have been counted. For example, a pre-specified number can be set to 8 consecutive V-A intervals that have each met the condition set forth in block 204. If the IMD 16 processor 80 determines that each monitored V-A interval satisfies Vp-As<Time1, then the YES path from block 206 continues to block 208 in which PMT is suspected. In contrast, the NO path from block 206 causes the computer instructions executed by the IMD 16 processor 80 to return to block 202 and continue monitoring RV-RA intervals. The NO path indicates less than pre-specified consecutive number of VA intervals has been counted. Any Vs event, atrial pace (Ap) event or refractory atrial sensed event (Ar) that occurs before a suspected PMT state causes a return to detection of looking for 8 consecutive As-Vp<400 ms.

At block 210, the IMD 16 processor measures and records a first VA interval. All data is stored into the memory of the IMD 16. An exemplary VA interval could be 500 ms.

Figure 6:
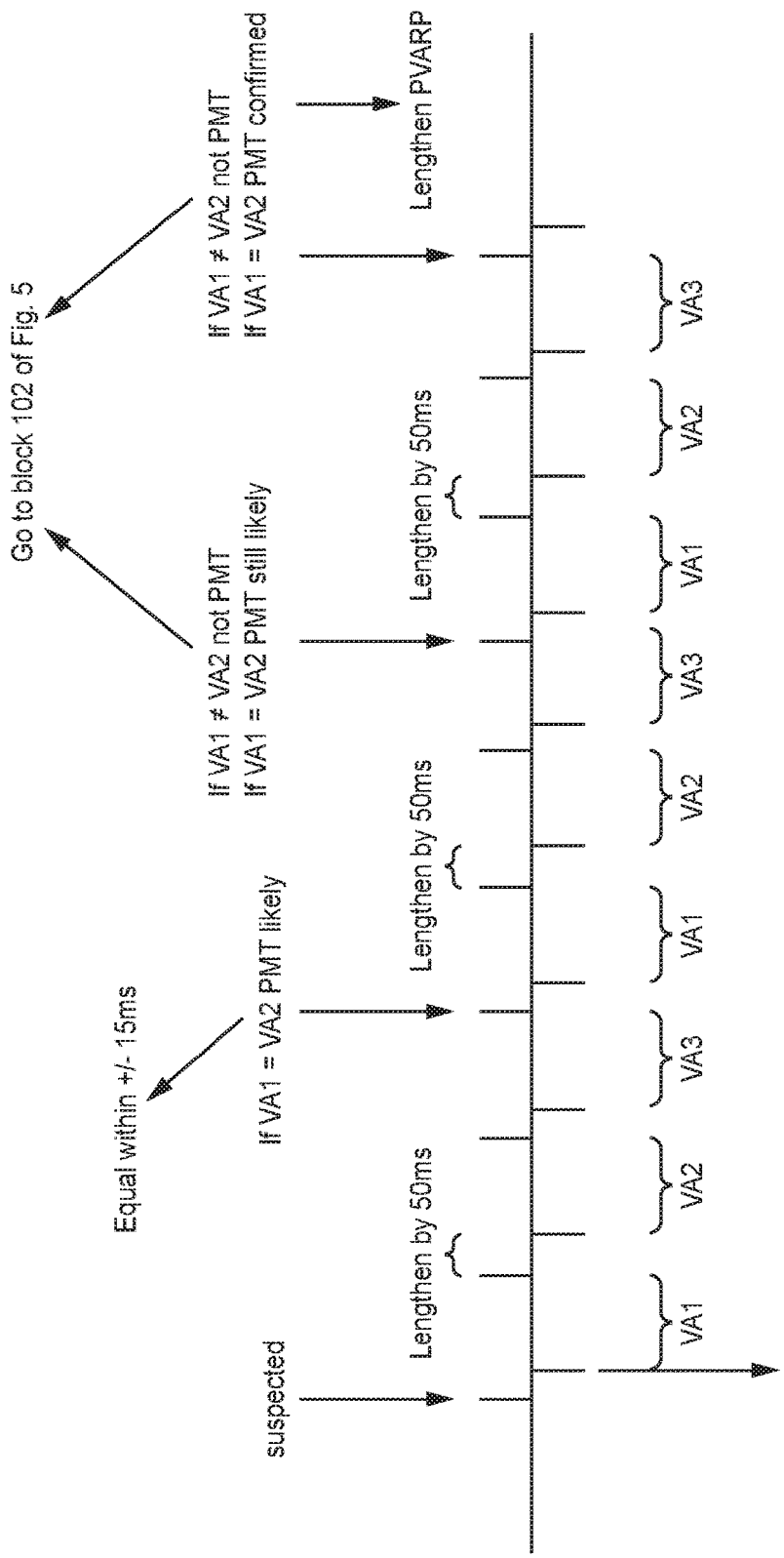
FIG. 6 is an event timing diagram that generally depicts atrial events and ventricular events with suspected and confirmed PMTs.

At block 212, the IMD 16 processor 80 is configured to adjust SAV interval. For example, the SAV duration can be lengthened or extended a certain amount of time. By way of illustration, the SAV can be extended by up to 50 ms, as shown in FIG. 6.

At block 214, the IMD 16 processor 80 is configured to measure and record a second VA interval. An exemplary VA interval could be 400 ms.

At block 216, the IMD 16 processor 80 is configured to return to a normal SAV interval. A normal SAV interval is a programmed SAV for a particular patient. The normal SAV can be pre-programmed into the IMD 16. Block 218, optionally, the IMD 16 processor measures and records a third VA interval for another comparison with the VA1 interval to further ensure that a PMT was detected.

At block 220, the IMD 16 processor is configured to compare first VA (i.e. VA1) and second VA (i.e. VA2) to each other for the purpose of determining whether VA1=VA2.

Figure 8:
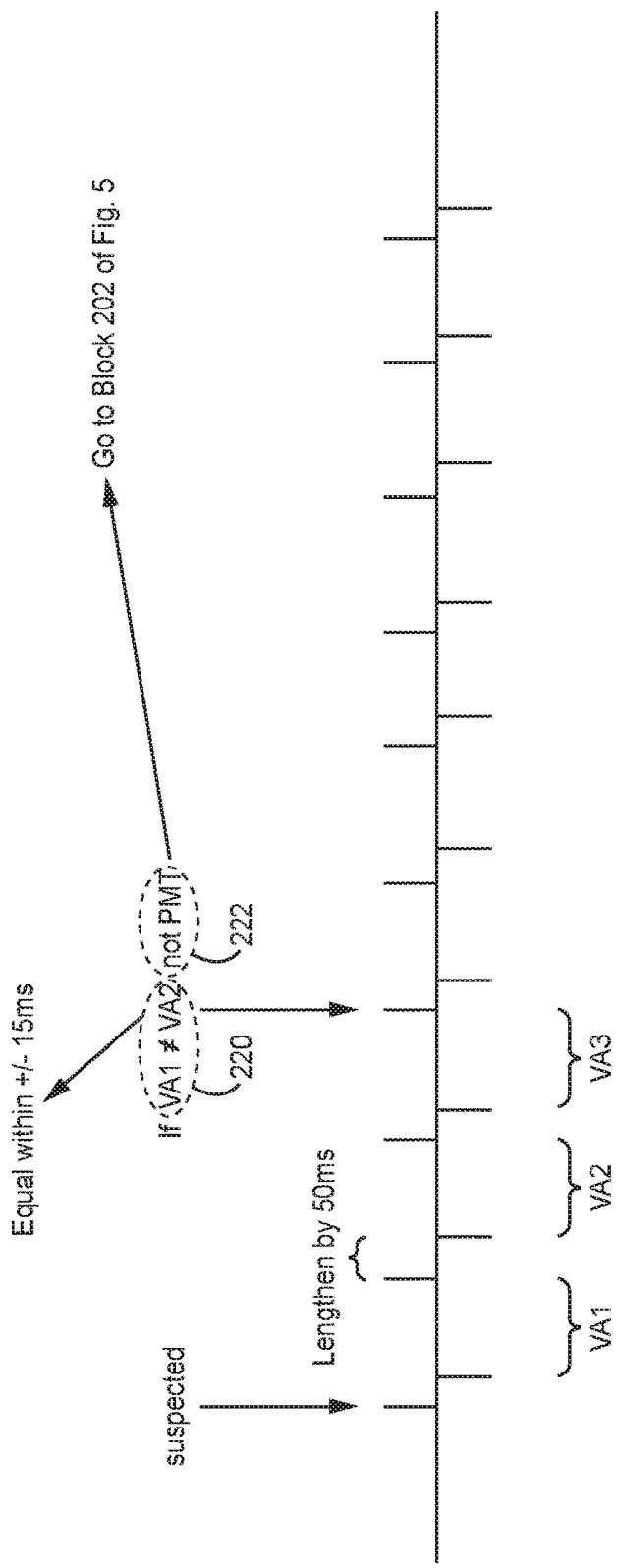
FIG. 8 is an event timing diagram that generally depicts VA1, VA2 and VA3 intervals and lengthening the AV interval by 50 ms.

Referring briefly to FIG. 6 and FIG. 8, if VA1=VA2 then PMT is likely present. In contrast, VA1≠VA2 then PMT is not likely to be present. Generally, some tolerance can be applied when evaluating the equivalence of VA1 and VA2. For example, when determining whether VA1 and VA2 are substantially equivalent, processor 80 is configured to declare VA1=VA2 if a range of having a tolerance of plus or minus 15 ms exists when subtracting VA1 from VA2.

Optionally, method 200 can also check whether VA1=VA3 as an additional check for higher specificity. Exemplary VA1 interval, VA2 interval, and VA3 interval are shown in FIG. 6.

At block 222, a determination is made as to whether a PMT is still suspected using the conditions set forth at block 220. For example, if VA1=VA2, a PMT is suspected. VA1=VA2 within a 15 ms range. In contrast, if VA1≠VA2 a PMT is not confirmed to be present.

The YES path from block 222 continues to block 224. At block 224, the IMD 16 processor determines whether a loop returning to block 210 is repeated a certain number of times. For example, the computer instructions require that the loop of block 224 to block 210 must continue a pre-specified number of times. The pre-specified number of times can be set to three times. If less than the pre-specified number of times of loops has occurred, the NO path returns to block 210.

At block 226, the IMD 16 processor determines a PMT is confirmed. If the PMT is confirmed, then the YES path continues to block 228 in which the PVARP prespecified cycle is adjusted. For example, the PVARP is extended, as is shown in FIG. 6. If a PMT is not confirmed, then the NO path continues to return path block 202.

At block 230, the IMD 16 processor 80 employs a timer to ensure a pre-specified amount of time (i.e. X time in block 230) is allowed to expire before the algorithm set forth in method 200 is restarted by returning to block 202 of FIG. 5 for continued monitoring of RV-RA intervals.

Method 200, as implemented by processor 80, appropriately confirms a PMT and then extends or lengthens the duration of PVARP to ensure proper timing occurs between the atrial events and ventricular events thereby allowing the heart to return to normal rhythm. Additionally, confirming a PMT through method 200 avoids inappropriate PMT intervention (e.g. extending post-ventricular atrial refractory period (PVARP) for one cycle) which can lead to dropped beats or the interruption of CRT pacing.

The techniques described in this disclosure, including those attributed to the IMD, programmer, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Various examples have been described for detecting PMT via a subcutaneous implantable cardioverter defibrillator and/or a leadless pacing device.

An example of a subcutaneous configuration that may implement the present disclosure is depicted and described in US 2015-0142069 A1, entitled Systems and Methods For Leadless Cardiac Resynchronization Therapy, filed on Feb. 5, 2014, and assigned to the assignee of the present invention, the disclosure of which is incorporated by reference in its entirety.

In summary, the present disclosure is able to confirm whether a PMT is actually present thereby optimizing delivery of pacing therapy. For example, If 8 consecutive Vp-As intervals are <400 ms, PMT is suspected. If lengthening the SAV does not change the VP-AS interval, PMT is confirmed. Generally, the IMD 16 processor 80 executes the following computer instructions to confirm PMT:

Measure Vp-As (VA1)
    Lengthen SAV by 50 ms for 1 beat
    Measure Vp-As (VA2)
    Return to normal SAV
    Measure Vp-As (VA3)
    If VA1≠VA2, not PMT—exit the PMT confirmation algorithm. (optionally also check to confirm VA1=VA3)
    If VA1=VA2, PMT is likely
    Repeat measurement cycle two times (6 more beats) to confirm PMT If Vs occurs any time a Vp is expected, the detection of PMT algorithm is exited. When PMT is confirmed, the PVARP is extended to 400 ms for 1 beat. Any further interventions is suspended for 85 seconds. Extending PVARP only when a true PMT is present minimizes disruption to pacing therapy.

SUMMARY OF ILLUSTRATIVE EMBODIMENTS

The following paragraphs enumerated consecutively from 1 through 24 provide for various aspects of the present invention.

Embodiment 1 is a method that employs an implantable medical device to detect pacemaker mediated tachycardia (PMT) and adjust a parameter in response to detection of the PMT, the method comprising:
with a processor located in the implantable medical device,
  (1) measuring a first Vp-As (VA1),
  (2) lengthening a first sensed atrioventricular interval (SAV) by up to 50 ms to a second SAV for 1 beat in response to measuring VA1,
  (3) measuring a second Vp-As (VA2),
  (4) returning to a third SAV,
  (5) measuring a third Vp-As (VA3),
  (6) determining whether VA1=VA2 and VA1=VA3,
  (7) in response to determining whether VA1=VA2 and VA1=VA3, confirming presence of PMT, and
  (8) in response to confirming presence of PMT, the parameter is adjusted.

Embodiment 2 is a method of embodiment 1 wherein the parameter that is adjusted is extending post-ventricular atrial refractory period (PVARP).

Embodiment 3 is a method of embodiment 2 or 3 wherein PVARP is extended.

Embodiment 4 is a method of any of embodiments 2-3 wherein VA1 is considered about equal to VA2 within a range of +/−15 milliseconds.

Embodiment 5 is a method of any of embodiments 1-4, wherein PMT is not confirmed if VA1 does not equal VA2.

Embodiment 6 is a method of any of embodiments 1-5, wherein the measurement cycle is repeated a number of times to confirm detection of PMT.

Embodiment 7 is a method of embodiments 3-6, wherein in response to PMT being confirmed, a PVARP is extended to 400 ms for 1 beat.

Embodiment 8 is a method of embodiments 4-7 wherein PVARP is extended for 10 cycles.

Embodiment 9 is a method of embodiments 4-8 wherein PVARP is extended more than 1 cycle.

Embodiment 10 is a method of any of embodiments 1-9 wherein first and third SAVs are equal to each other.

Embodiment 11 is a system of employing an implantable medical device to detect pacemaker mediated tachycardia (PMT) and adjusting a parameter in response to detection of the PMT, the system comprising:
with a processor located in the implantable medical device,
  (1) measuring a first Vp-As (VA1),
  (2 lengthening SAV by 50 ms for 1 beat in response to measuring VA1,
  (3) measuring a second Vp-As (VA2),
  (4) returning to a normal SAV,
  (5) measuring a third Vp-As (VA3),
  (6) determining whether VA1=VA2,
  (7) in response to determining whether VA1=VA2, confirming presence of PMT,
  (8) in response to confirming presence of PMT, PVARP is extended.

Embodiment 12 is a system of any of embodiments 11 wherein the parameter that is adjusted is PVARP.

Embodiment 13 is a system of any of embodiments 11-12 wherein PVARP is extended.

Embodiment 14 is a system of any of embodiments 11-13 wherein VA1 is considered about equal to VA2 within a range of +/−15 milliseconds.

Embodiment 15 is a system of any of embodiments 11-14, wherein PMT is not confirmed if VA1 does not equal VA2.

Embodiment 16 is a system of any of embodiments 11-15, wherein the measurement cycle is repeated a number of times to confirm detection of PMT.

Embodiment 17 is a system of any of embodiments 12-16, wherein in response to PMT being confirmed, a PVARP is extended to 400 ms for 1 beat.

Embodiment 18 is a system of any of embodiment 11-17 wherein PVARP is extended for 10 cycles.

Embodiment 19 is a system of employing an implantable medical device to detect pacemaker mediated tachycardia (PMT) and adjust a parameter in response to detection of the PMT, the system comprising:
with a processor located in the implantable medical device, the processor providing a means for:
  (1) measuring a first Vp-As (VA1),
  (2) lengthening a first SAV by 50 ms for 1 beat in response to measuring VA1,
  (3) measuring a second Vp-As (VA2),
  (4) returning to a second SAV,
  (5) measuring a third Vp-As (VA3),
  (6) determining whether VA1=VA2 and VA1=VA3,
  (7) in response to determining whether VA1=VA2 and VA1=VA3, confirming presence of PMT,
  (8) in response to confirming presence of PMT, the parameter is adjusted.

Embodiment 20 is a system of embodiment 19 wherein the parameter that is adjusted is PVARP.

Embodiment 21 is a system of embodiment 20 wherein duration of PVARP is extended.

Embodiment 22 is a system of any of embodiments 20-21 wherein VA1 is considered about equal to VA2 within a range of +/−15 milliseconds.

Embodiment 23 is a system of any of embodiments 20-22 wherein first and third SAVs are equal to each other.

Embodiment 24 is a system of employing an implantable medical device to detect pacemaker mediated tachycardia (PMT) and adjust a parameter in response to detection of the PMT, the system comprising:
with a processor located in the implantable medical device, the processor configured to:
  (1) measure a first Vp-As (VA1),
  (2) lengthen a first SAV by 50 ms for 1 beat in response to measuring VA1,
  (3) measure a second Vp-As (VA2),
  (4) return to a second SAV,
  (5) determine whether VA1=VA2,
  (6) in response to determining whether VA1=VA2, confirm presence of PMT,
  (7) in response to confirming presence of PMT, PVARP duration is lengthened.

Any combination of the described operations or functions is contemplated. These and other examples are within the scope of the following claims.

What is claimed is:

1. An implantable medical device configured to detect pacemaker mediated tachycardia (PMT) comprising:
a sensing module configured to sense atrial events (As);
a signal generator configured to generate and deliver electrical ventricular stimulation pulses (Vp);
a processor coupled to the sensing module and the signal generator and configured to control the stimulation generator to deliver said ventricular stimulation pulses (Vp) on expiration of a defined SAV interval following said atrial events (As), the processor further configured to:
- (1) measure a first Vp-As interval (VA1) between a first Vp and a first As,
- (2) lengthen a subsequent SAV interval by a certain amount of time over the defined SAV interval for 1 cardiac cycle in response to measuring VA1,
- (3) subsequently measure a second Vp-As interval (VA2) between a second Vp and a second As,
- (4) determine whether VA1 is equal to VA2,
- (5) in response to determining that VA1 is equal to VA2, confirming presence of PMT,
- (6) in response to confirming presence of PMT, extending a post-ventricular atrial refractory period (PVARP) following a subsequent Vp by a pre-specified amount of time, and
- (7) in response to a failure to confirm presence of PMT, leaving the post-ventricular atrial refractory period (PVARP) following the subsequent Vp unchanged.

2. An implantable medical device of claim 1, wherein the steps 1-4 are repeated a number of times to confirm detection of PMT.

3. An implantable medical device of claim 1, wherein in response to PMT being confirmed, the PVARP is extended up to 400 ms for 1 cardiac cycle.

4. An implantable medical device of claim 1 wherein the PVARP is extended for up to 10 cardiac cycles.

5. An implantable medical device of claim 1 wherein the processor is further configured to:
- (a) measure a third Vp-As (VA3) between a third Vp and a third As,
- (b) determine whether VA1 is equal to VA3,
- (c) in response to determining whether VA1 is equal to VA3, providing additional confirmation of PMT.

6. An implantable medical device of claim 5 wherein the processor is configured to designate VA1 as equal to VA3 in response to determining that VA1 and VA3 differ by less than a defined duration.

7. An implantable medical device of claim 1 wherein the subsequent SAV interval is lengthened up to 50 ms.

8. An implantable medical device of claim 1 wherein the processor is configured to designate VA1 as equal to VA2 in response to determining that VA1 and VA2 differ by less than a defined duration.

9. An implantable medical device of claim 8 wherein the processor is configured to designate VA1 as equal to VA2 in response to determining that VA1=VA2 a range of +/−15 milliseconds.

10. A system to detect pacemaker mediated tachycardia (PMT) comprising:
- sensing means for sensing atrial events (As);
- signaling means for generating and delivering electrical ventricular stimulation pulses (Vp);
- processing means for controlling the sensing means to deliver said ventricular stimulation pulses (Vp) on expiration of a defined SAV interval following said atrial events (As), the processing means further configured to:
  - (1) measure a first Vp-As interval (VA1) between a first Vp and a first As,
  - (2) lengthen a subsequent SAV interval by a certain amount of time over the defined SAV interval for 1 cardiac cycle in response to measuring VA1,
  - (3) subsequently measure a second Vp-As interval (VA2) between a second Vp and a second As,
  - (4) determine whether VA1 is about equal to VA2,
  - (5) in response to determining whether that VA1 is about equal to VA2, confirming presence of PMT,
  - (6) in response to confirming presence of PMT, extending a post-ventricular atrial refractory period (PVARP) following a subsequent Vp by a pre-specified amount of time, and
  - (7) in response to a failure to confirm presence of PMT, leaving the post-ventricular atrial refractory period (PVARP) following the subsequent Vp unchanged.

11. A system of claim 10, wherein the steps 1-4 are repeated a number of times to confirm detection of PMT.

12. A system of claim 10, wherein in response to PMT being confirmed, the PVARP is extended up to 400 ms for 1 cardiac cycle.

13. A system of claim 10 wherein PVARP is extended for up to 10 cardiac cycles.

14. An implantable medical device of claim 10 wherein the processor is configured to designate VA1 as equal to VA2 in response to determining that VA1 and VA2 differ by less than a defined duration.

15. A system of claim 14 wherein the processing means is configured designate VA1 as equal to VA2 in response to determining that VA1=VA2+/−15 milliseconds.

16. A method of employing an implantable medical device to detect pacemaker mediated tachycardia (PMT) and adjust a parameter in response to detection of the PMT, the method comprising:
- with a processor located in the implantable medical device,
  - the processor configured to deliver ventricular stimulation pulses (Vp) on expiration of a defined SAV interval following sensed atrial events (As), the processor further configured to:
    - (1) measure a first Vp-As interval (VA1) between a first Vp and a first (As),
    - (2) lengthen a subsequent SAV interval by a certain amount of time over the defined SAV interval for 1 beat in response to measuring VA1,
    - (3) subsequently measure a second Vp-As (VA2),
    - (4) determine whether VA1 is about equal to VA2,
    - (5) in response to determining VA1 is equal to VA2, confirming presence of PMT,
    - (6) in response to confirming presence of PMT, lengthening a post-ventricular atrial refractory period (PVARP) following a subsequent Vp by a pre-specified amount of time, and
    - (7) in response to a failure to confirm presence of PMT, leaving the post-ventricular atrial refractory period (PVARP) following the subsequent Vp unchanged.

17. The method of claim 16, wherein the cycle is the steps 1-4 are repeated a number of times to confirm detection of PMT.

18. The method of claim 16, wherein in response to PMT being confirmed, the PVARP is lengthened to 400 ms for 1 cardiac cycle.

19. The method of claim 18 wherein PVARP is lengthened for up to 10 cardiac cycles.

20. An implantable medical device of claim 16 wherein the processor is configured to designate VA1 as equal to VA2 in response to determining that VA1 and VA2 differ by less than a defined duration.

21. The method of claim 20 wherein VA1 is considered equal to VA2 if VA1=VA2+/−15 milliseconds.

22. A method of employing an implantable medical device to detect pacemaker mediated tachycardia (PMT) and adjust a parameter in response to detection of the PMT, the method comprising:

sensing atrial events (As) with a sensing module coupled to a processor;

generating and delivering electrical ventricular stimulation pulses (Vp) by a signal generator coupled to the processor, the processor configured to control the stimulation generator to deliver said ventricular stimulation pulses (Vp) on expiration of a defined SAV interval following said atrial events (As), the processor further configured to:
(1) measure a first Vp-As interval (VA1) between a first Vp and a first Vs,
(2) lengthen a subsequent SAV interval by a certain amount of time over the defined SAV interval for 1 cardiac cycle in response to measuring VA1,
(3) subsequently measure a second Vp-As (VA2) between a second Vp and a second Vs,
(4) determine whether VA1 is equal to VA2,
(5) in response to determining that VA1 is equal VA2, confirming presence of PMT, and
(6) in response to confirming presence of PMT, lengthening a post-ventricular atrial refractory period (PVARP) following a subsequent Vp by a pre-specified amount of time, and
(7) in response to a failure to confirm presence of PMT, leaving the post-ventricular atrial refractory period (PVARP) following the subsequent Vp unchanged.

23. An implantable medical device of claim 22 wherein the processor is configured to designate VA1 as equal to VA2 in response to determining that VA1 and VA2 differ by less than a defined duration.

* * * * *